(12) United States Patent
Karpiel et al.

(10) Patent No.: US 6,692,484 B1
(45) Date of Patent: Feb. 17, 2004

(54) DEVICES FOR EXTRACTING BILIARY OR URINARY STONES

(75) Inventors: John A. Karpiel, Winston-Salem, NC (US); Giuseppe Lombardo, Largo, FL (US); Samuel Jakovljevic, Hertfordshire (GB)

(73) Assignee: Wilson-Cook Medical Incorporated, Winston-Salem, NC (US)

( * ) Notice: Subject to any disclaimer, the term of this patent is extended or adjusted under 35 U.S.C. 154(b) by 191 days.

(21) Appl. No.: 09/615,017

(22) Filed: Jul. 13, 2000

Related U.S. Application Data

(60) Provisional application No. 60/144,551, filed on Jul. 17, 1999.

(51) Int. Cl.$^7$ .............................................. A61M 27/00
(52) U.S. Cl. ................. 604/544; 604/540; 604/101.01; 604/104; 600/31; 606/191
(58) Field of Search ................. 604/544, 540, 604/101.01, 101.05, 103.06, 103.07, 103.08, 104; 600/31; 128/1 R, 328; 606/191, 200

(56) References Cited

U.S. PATENT DOCUMENTS

| | | | | |
|---|---|---|---|---|
| 4,295,464 A | | 10/1981 | Shihata | ........................ 128/1 R |
| 4,469,100 A | | 9/1984 | Hardwick | .................... 128/328 |
| 4,627,837 A | | 12/1986 | Gonzalo | ...................... 604/101 |
| 4,781,677 A | | 11/1988 | Wilcox | .......................... 604/28 |
| 4,911,163 A | * | 3/1990 | Fina | ............................ 606/127 |
| 4,930,496 A | * | 6/1990 | Bosley, Jr. | ...................... 601/4 |

(List continued on next page.)

FOREIGN PATENT DOCUMENTS

| | | |
|---|---|---|
| DE | 1069823 | 11/1959 |
| EP | 0200668 | 11/1986 |

(List continued on next page.)

OTHER PUBLICATIONS

Quantum TTC® Biliary Balloon Dialtors; Wilson–Cook Medical, Inc., Winston–Salem, NC; Catalog (date unknown).

(List continued on next page.)

*Primary Examiner*—Thomas Denion
*Assistant Examiner*—Ching Chang
(74) *Attorney, Agent, or Firm*—Brinks Hofer Gilson & Lione

(57) ABSTRACT

A device (10) for extracting biliary or urinary stones, calculi or the like (stones 104) from the biliary or urinary tract (100) of a patient including a catheter shaft (12), a first expandable apparatus for dilating the tract entrance or the sphincter thereat, and a second expandable apparatus for capturing the stone and/or urging it out of the tract. The first expandable apparatus may be an inflatable balloon (14) fixed on the catheter shaft (12), and the second expandable apparatus may be a second inflatable balloon (18) fixed on the catheter shaft or on a second tube telescopically associated with the catheter shaft, or may be a reversibly collapsible extraction basket (154) such as of nitinol wires, that is slidably receivable in and extendable from the catheter shaft (112). A device (210) for temporarily dilating a sphincter in a patient, such as the Sphincter of Oddi (102), includes an elongated catheter shaft (212) and an inflatable balloon (264) carried thereon and having a proximal portion (266), a distal portion (268) and an intermediate portion (270) therebetween. The intermediate balloon portion (270) has, upon inflation of the balloon (264), a diameter suited for temporary dilation of the Sphincter (102), while the proximal and distal balloon portions (266 and 268) have, upon inflation of the balloon (264), diameters greater than the inflated diameter of the intermediate balloon portion (270).

28 Claims, 6 Drawing Sheets

U.S. PATENT DOCUMENTS

| | | | | |
|---|---|---|---|---|
| 5,024,617 A | | 6/1991 | Karpiel | 606/47 |
| 5,129,910 A | * | 7/1992 | Phan et al. | 606/127 |
| 5,152,772 A | * | 10/1992 | Sewell, Jr. | 604/22 |
| 5,176,619 A | * | 1/1993 | Segalowitz | 600/18 |
| 5,334,143 A | * | 8/1994 | Carroll | 604/514 |
| 5,383,849 A | | 1/1995 | Johlin, Jr. | 604/53 |
| 5,484,384 A | * | 1/1996 | Fearnot | 600/3 |
| 5,643,199 A | | 7/1997 | Rowland et al. | 604/22 |
| 5,741,271 A | * | 4/1998 | Nakao et al. | 604/523 |
| 5,752,971 A | * | 5/1998 | Rosenbluth et al. | 606/192 |
| 5,836,951 A | * | 11/1998 | Rosenbluth et al. | 606/108 |
| 5,868,698 A | * | 2/1999 | Rowland et al. | 604/22 |
| 5,908,435 A | * | 6/1999 | Samuels | 606/200 |
| 5,924,175 A | * | 7/1999 | Lippitt et al. | 24/537 |
| 5,935,139 A | * | 8/1999 | Bates | 606/159 |
| 5,989,266 A | | 11/1999 | Foster | 606/127 |
| 6,027,475 A | * | 2/2000 | Sirhan et al. | 604/96.01 |
| 6,053,934 A | | 4/2000 | Andrews et al. | 606/207 |
| 6,056,719 A | * | 5/2000 | Mickley | 604/96.01 |
| 6,068,610 A | * | 5/2000 | Ellis et al. | 604/96.01 |
| 6,099,534 A | * | 8/2000 | Bates et al. | 606/127 |
| 6,174,318 B1 | * | 1/2001 | Bates et al. | 606/113 |

FOREIGN PATENT DOCUMENTS

| | | |
|---|---|---|
| FR | 2380018 | 9/1978 |
| WO | 9741782 | 11/1997 |
| WO | 9825656 | 6/1998 |

OTHER PUBLICATIONS

Quantum TTC™ Biliary Balloon Dialtors; Wilson–Cook Medical, Inc., Winston–Salem, NC; Catalog (date unknown).

Tri–ex™ Triple Lumen Extraction Balloon; Wilson–Cook Medical, Inc., Winston–Salem, NC; Catalog (1996).

The WEB™ Extraction Basket: Wilson–Cook Medical, Inc., Winston–Salem, NC; Catalog (date unknown).

* cited by examiner

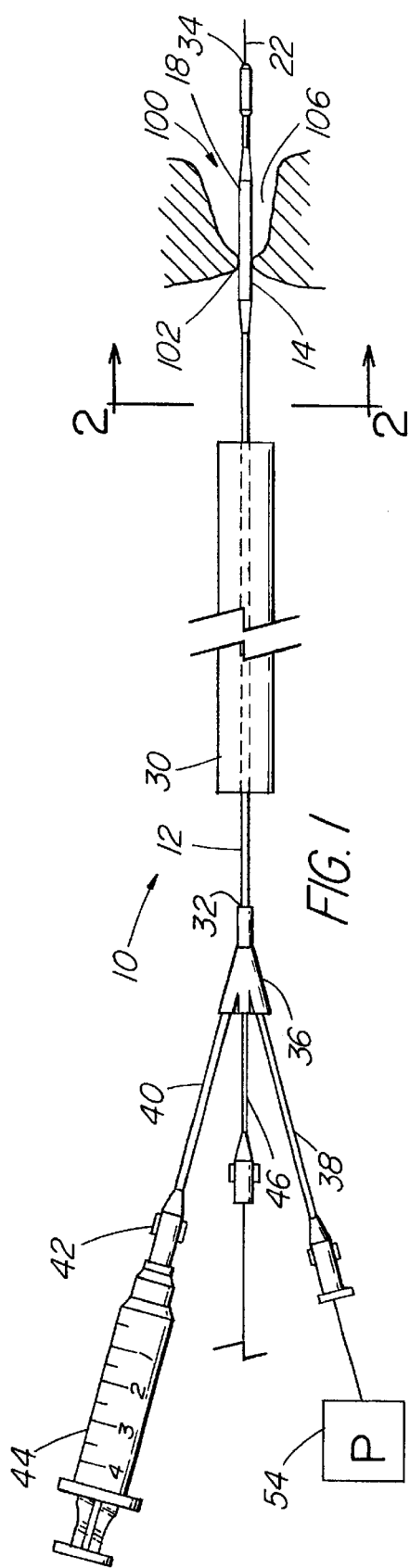
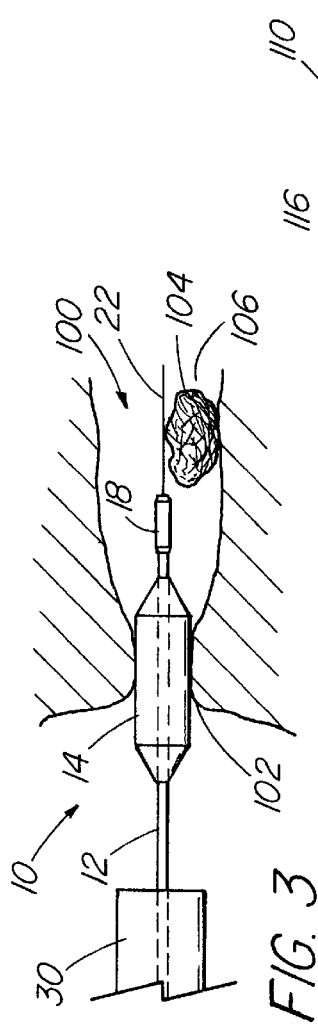
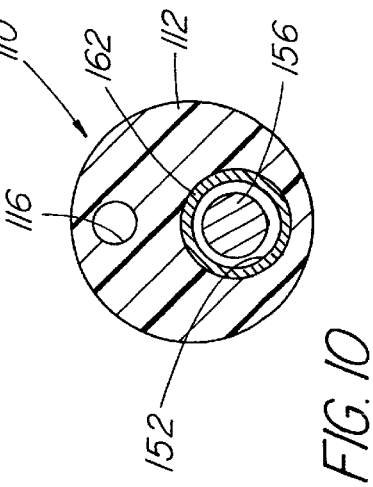
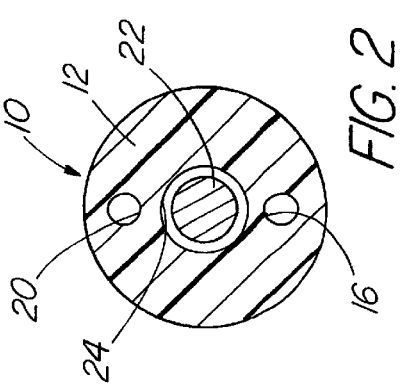
FIG. 1
FIG. 3
FIG. 10
FIG. 2

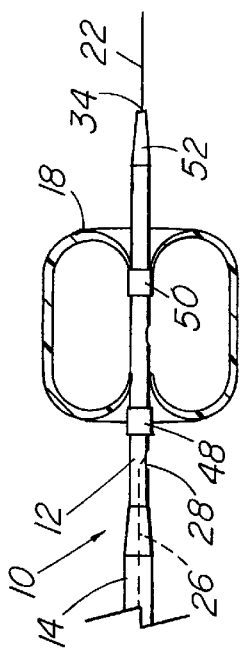
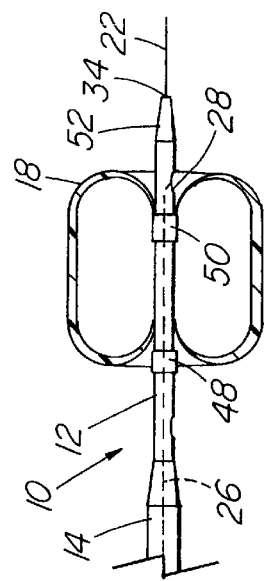
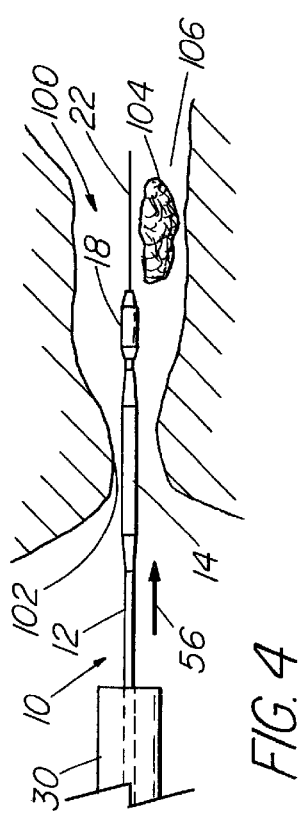
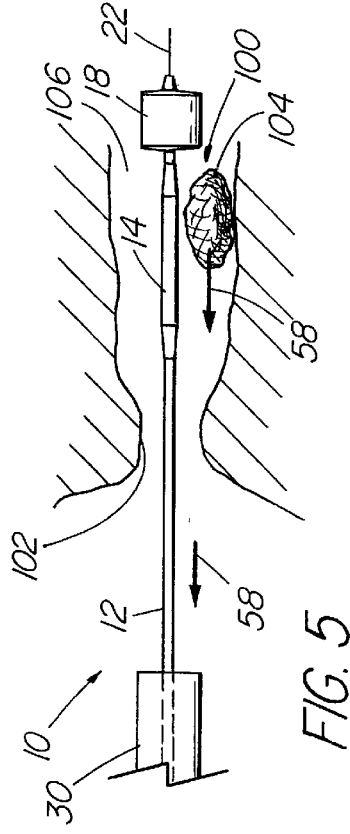
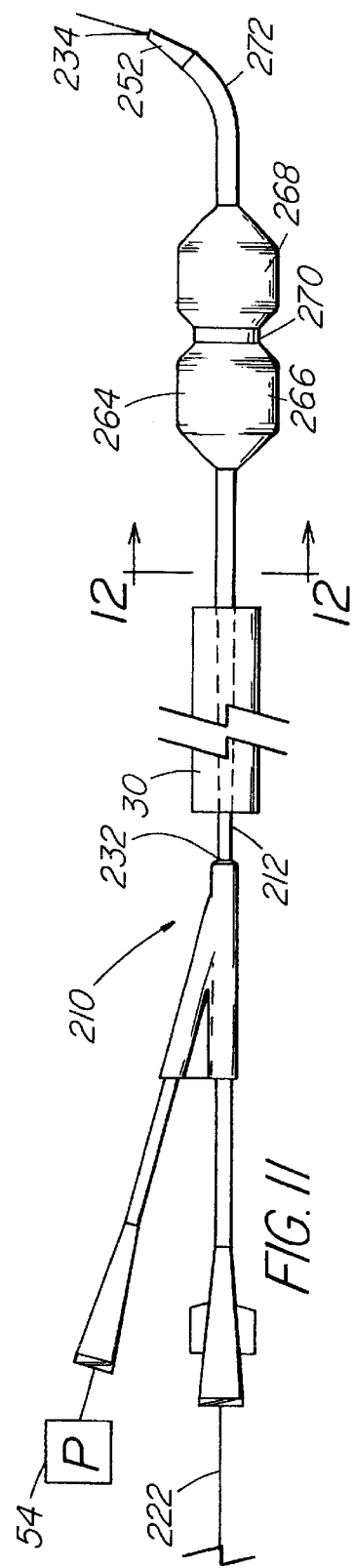

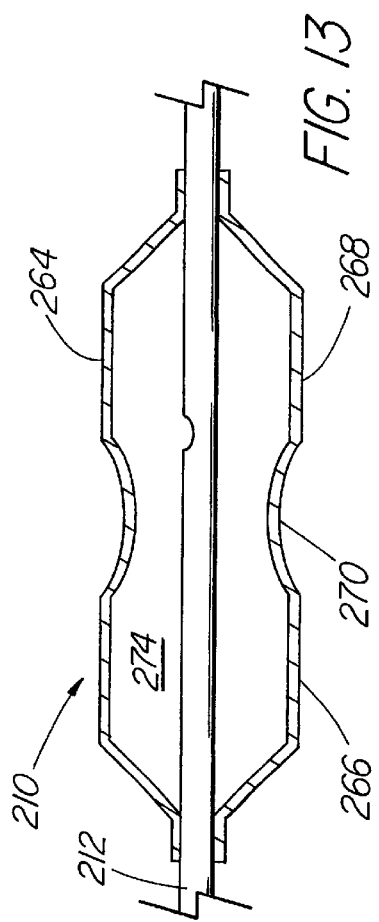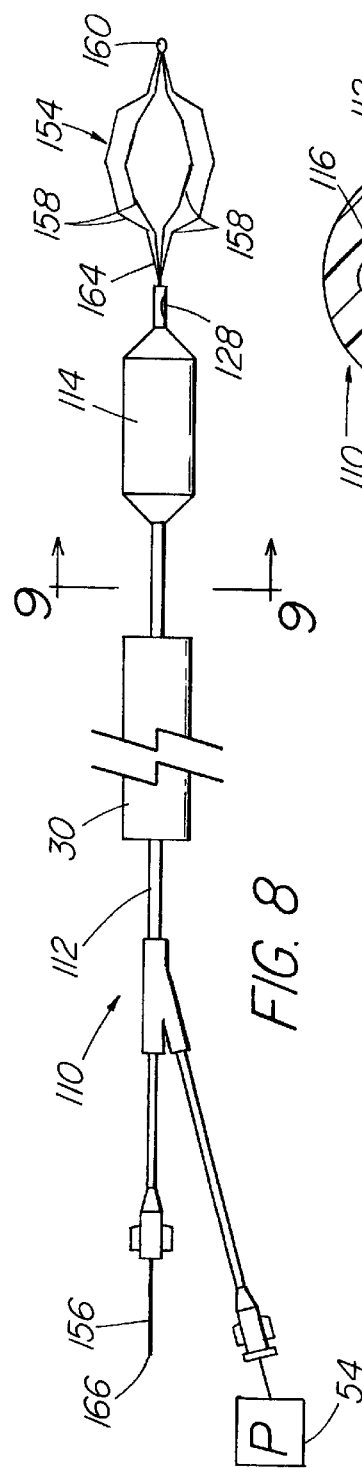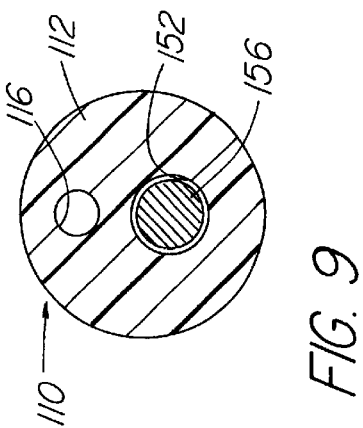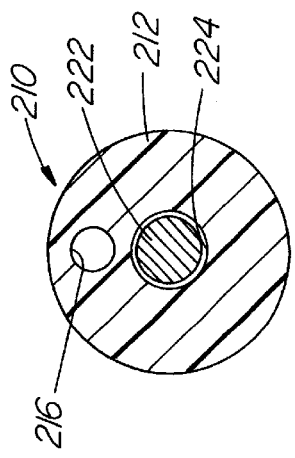

DEVICES FOR EXTRACTING BILIARY OR URINARY STONES

CROSS-REFERENCE TO RELATED APPLICATIONS

This application claims priority of Provisional Application No. 60/144,551 filed Jul. 17, 1999.

TECHNICAL FIELD

This invention relates generally to medical devices, and more particularly to devices for engaging and extracting or removing stones, calculi or the like from the biliary or urinary tracts.

BACKGROUND OF THE INVENTION

A variety of tracts or ducts in the body are subject to the development of stones, calculi or the like. (For convenience, such stones, calculi and the like may sometimes be referred to herein by the words "stone" or "stones". For example, stones may develop in the kidneys and migrate down the ureters. Sometimes such stones become lodged in the ureters, requiring surgical intervention for their removal. Similarly, gallstones may develop in the gallbladder, and migrate down the biliary duct (the common bile duct), through the ampulla of Vater, and out the Sphincter of Oddi into the duodenum. As with kidney stones, such stones occasionally become lodged in the biliary duct, the pancreatic duct or the ampulla of Vater. Indeed, gallstones can be of such a size as to be unable to pass through the Sphincter of Oddi. In either case, surgical intervention is again required for their removal.

A number of surgical devices are known for engaging and extracting or removing stones from the biliary or urinary tracts. However, the satisfactory introduction of such devices into the ampulla of Vater or the associated ducts may require the surgical cutting of the papilla of Vater (in which the Sphincter of Oddi is formed). Such cutting is commonly performed with sphincterotomes, in particular, papillotomes. Such cutting devices are typically used in conjuction with an endoscope.

A very useful papillotome is disclosed in U.S. Pat. No. 5,024,617 (J. Karpiel, Jun. 18, 1991). The specification of the patent notes that a survey conducted by the American Society for Gastrointestinal Endoscopy revealed that the most common major complication from endoscopic sphincterotomy was bleeding. The specification of the patent further notes that the vast majority of such bleeding typically results when the retroduodenal artery is cut. Other major complications include pancreatitis, perforation and cholangitis. The device disclosed in the patent is intended to enhance the control a physician has while performing a sphincterotomy, and thereby reduce the risk of such injury to the patient from the procedure. While the device disclosed in the patent appears to achieve this desired reduction in risk, healing of the papilla of Vater after cutting can be problematic. Moreover, the physical arrangement of useful surgical cutters may hinder visualization of the site being cut. Further, U.S. Pat. No. 5,383,849 (F. Johlin, Jr., Jan. 24, 1995) notes that, when a cannula is used in endoscopic retrograde cholangiopancreatography (ERCP), difficulty is sometimes encountered in the attempt to successfully cannulate (that is, enter with a cannula) the desired duct among the bile and pancreatic ducts.

Attempts have been made to avoid the problems associated with cutting of the papilla of Vater. For example, catheter devices including inflatable balloons have been used to temporarily dilate the Sphincter of Oddi (or other biliary structure) so as to permit the passage of retrieval baskets or extraction balloons therethrough. One such biliary balloon dilator is sold by Wilson-Cook Medical Inc., Winston-Salem, N. C., under the name Quantum TTC®. That dilator includes a biliary dilation balloon carried on a dual-lumen catheter, one lumen serving for the introduction of an inflation medium into the dilation balloon, and the other lumen accepting a conventional 0.89 mm (0.035 in.) guide wire therein. An associated apparatus (the Quantum Biliary Inflation Device, or Q.B.I.D.™) is used to control the inflation pressure or inflation volume of the balloon.

During use, the deflated balloon of the device is first positioned via an endoscope across the structure to be dilated, for example, across the Sphincter of Oddi, and then inflated to dilate the structure. The balloon is then deflated and removed from the structure, and the device removed from the patient. It has been found that the Sphincter of Oddi remains dilated for a few minutes before it closes; during the time it is dilated, a retrieval basket or extraction balloon is introduced through the endoscope and through the dilated Sphincter, into engagement with the stones to be removed.

An example of an extraction balloon device useful for this purpose is the Tri-Ex™ Triple Lumen Extraction Balloon sold by Wilson-Cook Medical Inc. The device includes a triple lumen catheter which carries on it a distending latex balloon. One lumen serves to deliver an inflation medium to the balloon, a second serves to contain a conventional guide wire, and a third permits the introduction of a contrast medium distal (above) or proximal (below) the balloon. The volume of inflation medium is determined by a premeasured syringe connected to the first lumen. In use, the deflated balloon of the device is introduced through the Sphincter of Oddi (for example, via the endoscope) past the stones, then inflated and employed to urge the stones towards and out the Sphincter of Oddi. Other retrieval balloons are of course useful for this purpose as well.

A variety of retrieval baskets are known for the endoscopic removal of stones and other foreign bodies from both the biliary and urinary tracts. Such baskets can be exemplified by the WEB™ Extraction Basket sold by Wilson-Cook Medical Inc., which includes a plurality of filaments or wires constructed of a shape memory material. Nitinol in a superelastic state is an example of a shape memory material. As a further example, U.S. Pat. No. 4,295,464 (A. A. Shihata, Oct. 20, 1981) discloses a ureteric stone extractor having two ballooned catheters, in particular, an inner dislodger catheter slidable within a relatively larger outer dilator catheter. The dislodger catheter includes a lumen having a stiffening metal stylet disposed in it. The balloon of the dilator catheter must remain inflated during use of the extractor, thus preventing visualization of the stone by an endoscope.

Unfortunately, the successful use of many of such devices is often not possible. In particular, the closure time of the papilla of Vater (that is, the time in which the Sphincter of Oddi closes after dilation by the balloon) is so short that the Sphincter of Oddi often closes before the dilation balloon catheter is removed from the patient and the retrieval basket or extraction balloon is introduced and advanced to the Sphincter. Even when the guide wire has been advanced through the Sphincter, cannulation of the extraction balloon through the collapsed Sphincter may still be difficult. Moreover, guide wires are not generally used with retrieval baskets; unless the basket is introduced quickly enough, the dilation of the Sphincter is a wasted effort. Further, since the dilation balloon is typically axially aligned with the line-of-sight of the endoscope, ensuring that the balloon actually lies across the Sphincter of Oddi or other structure may be difficult as well.

It would be highly advantageous to have devices which permitted the engagement and extraction or removal of stones, calculi or the like from the biliary tract, the urinary tract or other body structure without requiring any surgical cutting of body tissue. It would also be highly advantageous to have devices which permitted the introduction of a retrieval basket, extraction balloon or the like quickly enough to take advantage of the time the Sphincter of Oddi or other structure remained dilated, so as to permit the ready passage of the basket or balloon through the Sphincter and allow the ready observation of the engagement of the stones by the basket or balloon via the endoscope. It would further be highly advantageous to have devices which permitted the basket, balloon or the like to urge the stones through the Sphincter of Oddi or other structure while it was still dilated. Finally, it would be highly advantageous to have dilation balloon devices which affirmatively ensured the position of the dilation balloon with respect to the Sphincter of Oddi or other body structure during its dilation.

SUMMARY OF THE INVENTION

The foregoing problems are solved and a technical advance is achieved in illustrative devices for dilating sphincters or other structures in the body of a human or veterinary patient, and engaging and extracting or removing stones, calculi or the like (hereinafter, "stones") from the body of a human or veterinary patient, for example, from the biliary or urinary tract of the patient. The purpose of the device is to provide firstly means of dilating a sphincter or tract opening, and secondly means of extracting or retrieving stones from a tract beyond the sphincter or opening. Thus, in the present invention, a device comprises a catheter shaft, a first expandable apparatus fixed on the catheter shaft for dilating the tract entrance, and a stone retrieving apparatus associated with the catheter shaft for urging the stone through the tract entrance. The stone retrieving apparatus may be a second expandable apparatus. Either (or both) of the first and second expandable apparatus may be a balloon or may be a basket or cage. Both may be balloons, each on a discrete tube in a telescoping arrangement, or upon a single catheter device. The first expandable apparatus may be retained in the expanded position or condition during stone retrieval, or it may be deflated or collapsed and removed.

More particularly, in a first embodiment, the device of the present invention comprises a plural lumen catheter shaft which carries affixed to it both an appropriate inflatable dilation balloon, and a suitable inflatable retrieval balloon dimensioned and adapted for urging the stones through the biliary or urinary tract of the patient. Preferably, the dilation balloon is of nondistendable (nonstretchable) material, such as polyethylene terephthalate (PET), and the retrieval balloon is of distendable material, such as latex. Affixing both balloons to a single catheter shaft, as in the first embodiment, advantageously minimizes the profile of the device, advantageously minimizes the manipulative steps required for introduction and advancement of the device, and eliminates the time previously required to remove the dilation balloon from the patient and introduce a separate extraction balloon into the patient. The relatively small profile of the device readily allows the deflated balloons to be advanced along a previously inserted guide wire, for example, advanced through the Sphincter of Oddi or other structure or entrance to a small tract such as a ureter. When the dilation balloon lies fully across the Sphincter or other entrance, the dilation balloon is inflated so as to dilate the Sphincter or other entrance; the dilation balloon is then deflated so as to allow observation of the extraction balloon through the Sphincter or entrance via an endoscope. The extraction balloon is advanced until it has been moved to a position past the stones, and then is inflated and manipulated to urge the stones through the biliary or urinary tract of the patient.

This is not to say that the extraction balloon is itself employed to fully remove the stones from the patient. For example, with gallstones it is likely sufficient merely to urge the stones past the Sphincter of Oddi into the duodenum, and allow the stones to pass from the body naturally after that. Similarly, urging kidney stones from the ureters to the bladder is likely to be sufficient to ensure the subsequent elimination of the stones from the body. Moreover, it should be noted that, in general, it is anticipated that the endoscope will not pass through the Sphincter of Oddi or other structure; only the catheter shaft, dilation balloon and extraction balloon will.

In a second embodiment, the device of the present invention comprises a catheter shaft having a dilation balloon fixed on it, and a reversibly collapsible extraction basket slidably received in, and extendable from, the catheter shaft. The basket is preferably connected to a control member disposed in a lumen in the catheter shaft. The control member need not be a discrete member; for example, when the basket comprises a plurality of wires, the control member can comprise extending portions of the wires extending through the catheter shaft. While the device is preferably highly flexible, the basket and/or the control member provide sufficient stiffness to permit the basket (contained in the catheter shaft) and the deflated dilation balloon to be advanced through the Sphincter of Oddi or duct or ureter entrance until the balloon lies thereacross. The balloon is inflated to dilate the Sphincter or entrance, and then deflated to allow observation (via endoscope, through the dilated Sphincter or other structure) of the extension of the basket from the catheter shaft and into engagement with the stones. The stones are captured by the basket or otherwise urged by manipulation of the basket through the Sphincter of Oddi or entrance and into the digestive or urinary tract. Again, it is expected that, in general, the endoscope will not pass through the Sphincter of Oddi or entrance dilated.

In a third embodiment, the device of the present invention comprises a dumbbell-shaped or wasp-waisted balloon catheter for dilating a sphincter or duct or ureter entrance in a patient, preferably for dilating the Sphincter of Oddi. The device comprises an inflatable dilation balloon carried on a catheter shaft, the balloon having proximal and distal inflatable portions, and an intermediate inflatable portion between the proximal and distal portions. Unlike balloons previously used to anchor catheters in the body, all three portions of the dilation balloon are inflatable to a significant degree. More particularly, the intermediate inflatable portion of the balloon has an inflated diameter which is suited for the temporary dilation of the sphincter, while the proximal and distal inflatable portions have inflated diameters which are greater than the inflated diameter of the intermediate portion. Inflation of the balloon automatically centers the balloon in the sphincter, establishing a predetermined amount of dilation of the sphincter. The several portions of the balloon are preferably continuously formed, and are preferably in fluid communication with one another. Conveniently, the balloon defines a single inflation chamber, such that there are no walls or partitions separating the proximal, distal and intermediate portions of the dilation balloon. Separate inflation chambers in each of the several balloon portions are also contemplated within the present invention, of course.

A fourth embodiment provides two telescopically arranged tubes wherein the first tube is fitted with a first expandable apparatus for dilating a sphincter or duct or ureter entrance, and wherein the second tube is fitted with a second expandable apparatus for extracting or retrieving stones from the tract. The first tube may be inside or outside of the second tube. Either or both of the first and second expandable apparatus may be a balloon, a basket or a "cage". If the expandable apparatus are balloons, the first or dilator balloon is made of a nondeformable material that is capable of deforming the sphincter or tract opening when the balloon is inflated. The second or extraction balloon is made of a material that has to be deformable when the balloon is inflated to adapt to the tact in which the stones are located and to be able to withdraw the stones.

The telescopic arrangement of two tubes each having an expandable apparatus has also the advantage of minimizing the manipulative steps required for introduction and advancement of the device, and eliminates the time previously required to remove a dilation device from the patient and introduce a separate extraction balloon in the patient. The telescopic arrangement is therefore well suited to a situation where a sphincter, having been previously dilated, would collapse rapidly before a surgeon could proceed with the extraction of the stone.

Each of the embodiments of the device of the present invention is particularly advantageous over prior dilation and extraction devices in one or more of a variety of ways. For example, the devices of the present invention may permit the engagement and extraction or removal of stones, calculi or the like from the biliary tract, the urinary tract or other body structure without requiring any surgical cutting of body tissue, for example, of the Sphincter of Oddi. The devices of the present invention may also permit the introduction of an associated retrieval basket, extraction balloon or the like quickly enough to take advantage of the time the Sphincter of Oddi or tract entrance remained dilated, so as to permit the ready passage of the basket or balloon through the Sphincter and allow the ready observation of the engagement of the stones by the basket or balloon via the endoscope. The devices of the present invention may also permit their associated basket, balloon or the like to urge the stones through the Sphincter of Oddi or other entrance structure while it was still dilated. Finally, the devices of the present invention may affirmatively ensure the position of the dilation balloon with respect to the Sphincter of Oddi or other body structure during its dilation.

As indicated above, the device of the present invention possesses significant advantages over prior devices.

BRIEF DESCRIPTION OF THE DRAWINGS

A better understanding of the present invention will now be had upon reference to the following detailed description, when read in conjunction with the accompanying drawing, wherein like reference characters refer to like parts throughout the several views, and in which:

FIG. 1 is a side view of the preferred embodiment of the present invention;

FIG. 2 is a cross-sectional view taken along line 2—2 of FIG. 1;

FIGS. 3 through 5 are partial views of the embodiment of the present invention shown in FIG. 1;

FIG. 6 is a cross-sectional view of a portion of the preferred embodiment of the present invention shown in FIG. 1;

FIG. 7 is a cross-sectional view of another embodiment of the present invention, similar to FIG. 6;

FIG. 8 is a side view of another embodiment of the present invention;

FIG. 9 is a cross-sectional view taken along line 9—9 of FIG. 8;

FIG. 10 is a cross-sectional view of another embodiment of the present invention, similar to FIG. 9;

FIG. 11 is a side view of another embodiment of the present invention;

FIG. 12 is a cross-sectional view taken along line 12—12 of FIG. 11;

FIG. 13 is a cross-sectional view of a portion of the preferred embodiment of the present invention shown in FIG. 11;

DETAILED DESCRIPTION

Figure 14:
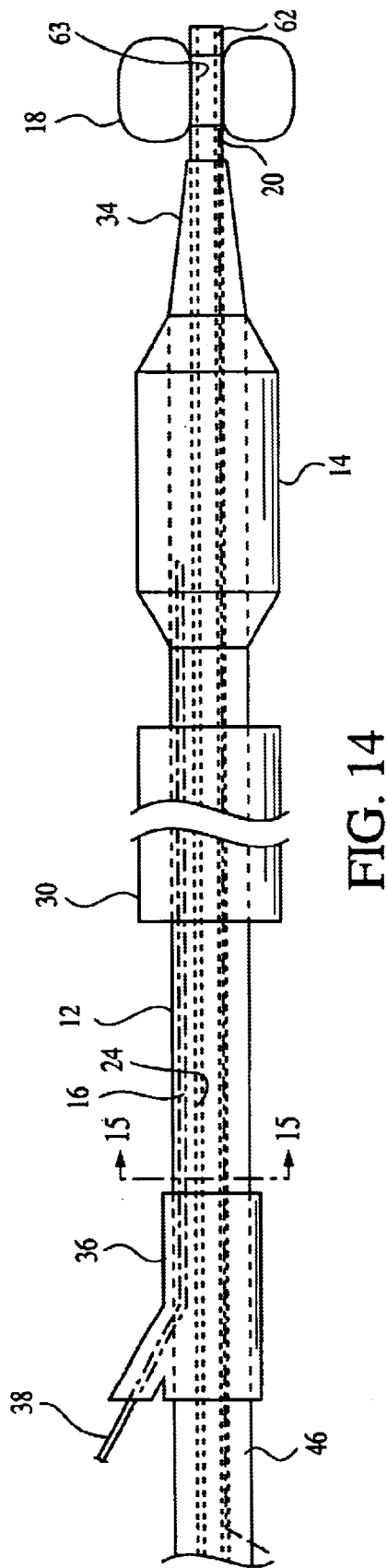
FIG. 14 is a cross-sectional view of another embodiment of the present invention, having telescoping tubes.

With reference first to FIGS. 1 and 2, an embodiment of a device 10 according to the present invention is thereshown, useful for extracting biliary or urinary stones, calculi or the like 104 (hereinafter, stone 104) from the biliary or urinary tract 100 of a patient. The device 10 and the other embodiments of the present invention are most preferably employed for temporary dilation of the Sphincter of Oddi 102 within the biliary tract 100, and will therefore be described with respect to a stone 104 located within the ampulla of Vater 106.

The device 10 of the present invention first comprises a catheter shaft 12 having a proximal end 32 and a distal end 34. The catheter shaft 12 preferably comprises silicone or another suitable medical grade material. When intended for use at the Sphincter of Oddi 102, the catheter shaft 12 is advantageously about 5 to about 7 French (1.67 to 2.33 mm) in size. Moreover, as explained in more detail below, when the device 10 is employed for engaging the stone 104 via an antegrade approach (that is, the device 10 is introduced into the patient through the patient's mouth), the catheter shaft 12 as advantageously about 180 to about 200 cm long.

The device 10 of the present invention also comprises a first inflatable balloon 14 fixed on the catheter shaft 12. The first balloon 14 is preferably dimensioned and adapted for the temporary dilation of a tract entrance, such as the Sphincter of Oddi, from an undilated diameter (FIG. 1) to a dilated diameter (FIG. 3), in a manner described in more detail below. To this end, the first balloon 14 is preferably about 3 to about 6 cm long, and is inflatable to a diameter of about 4 to about 10 mm. The first balloon 14 preferably comprises PET or another suitable medical grade materia such as irradiated polyethylene or polyimide.

The device 10 of the present invention further comprises a second inflatable balloon 18 fixed on the catheter shaft 12. The second balloon 18 is dimensioned and adapted for urging the stone 104 through the biliary or urinary tract 100 of the patient. Preferably, the second balloon 18 is dimensioned and adapted for urging the stone 104 through the Sphincter of Oddi 102, after temporary dilation of the Sphincter of Oddi 102 to its dilated diameter by inflation of the first balloon 14 and deflation of the first balloon 14, and before closure of the Sphincter of Oddi 102 to its undilated diameter. The second balloon 18 is preferably affixed to the catheter shaft 12 distal of the first balloon 14. The second balloon 18 advantageously comprises latex or another suitable medical grade material of comparable softness or elasticity such as silicone rubber. The selection of such other material for the second balloon 18 should be well within the skill of the art, for example, on a trial-and-error basis after considering softness or elasticity.

The second balloon 18 is preferably inflatable to a diameter about 2 to about 5 mm larger than the inflated diameter of the first balloon. A particularly preferred shape for the second balloon 18 is shown in cross-section in FIG. 6. When intended for use in engaging a stone 104 in the ampulla of Vater 106, the second balloon 18 is advantageously inflatable to a diameter of about 8 to about 15 mm, and to a volume of about 1.5 to about 4 cm$^3$. It is highly desirable that the device of the present invention be arranged to affirmatively establish a tension in the second balloon which is suitable for urging movement of the stones, calculi or the like, and minimize any risk of rupture of the second balloon from overpressure. For this purpose, the device 10 of the present invention preferably also comprises a structure 44 (FIG. 1) for delivery of a fixed, predetermined volume of inflation medium to the second balloon 18. The structure 44 can comprise the syringe shown in FIG. 1 or another suitable structure, such as the Wilson-Cook Q.B.I.D.™ apparatus.

The catheter shaft 12 of the device 10 of the present invention includes at least three (and preferably three) longitudinally extending lumens 16, 20 and 24 defined therein (FIG. 2). The first lumen 16 is dimensioned and adapted for the supply of a suitable inflation medium to the first balloon 14. The first lumen 16 is connected via a coupling 36 to an inlet 38 for the inflation medium, for example, supplied from a pressurized source 54 of the inflation medium. The second lumen 20 is similarly dimensioned and adapted for the supply of a suitable inflation medium to the second balloon 18. The second lumen 20 is connected via the coupling 36 to an inlet 40, connected in turn to the inflation medium delivery structure 44. (The inflation media for the first and second balloons 14 and 18 need not be the same, of course, and preferably may not be the same.) The third lumen 24 is dimensioned and adapted for receiving a guide wire 22 therein. The guide wire 22 can be a conventional 0.89 mm (0.035 in.) guide wire, or other guide wire suitable for the intended use of the device 10. The device 10 of the present invention can further comprise such a guide wire 22 receivable in the third lumen 24.

Imaging during use of the device 10 can be carried out in several ways. It is an important advantage of the present invention, however, that the stone 104 and the engagement of the second balloon 18 with the stone 104 can be viewed directly through the temporarily dilated Sphincter of Oddi 102. To this end, the device 10 is introduced into the patient via an endoscope, such as an over-the-wire endoscope 30 (shown only schematically), to which the catheter shaft 12 is connectable. Such connection occurs, for example, by feeding the catheter shaft 12 through the endoscope 30. The device 10 of the present invention can of course further comprise the endoscope 30.

Alternatively, depending upon the circumstances of use, it may be desirable to image the device 10 or the stone 104 by means of radioscopy, fluoroscopy or the like. Such circumstances may arise, for example, if the stone 104 is located some distance from the Sphincter of Oddi 102. The device 10 can further comprise at least one radiopaque band 48 or 50 (and preferably a pair of radiopaque bands 48 and 50) positioned on the catheter shaft 12 immediately proximal or distal of the second balloon, respectively. The radiopaque bands 48 and 50 can comprise a suitable metal or other medical grade material, and are shown in FIGS. 6 and 7.

Similarly for imaging, the device 10 of the present invention can also or alternatively comprise a fourth longitudinally extending lumen 26 defined in the catheter shaft 12 (see FIGS. 6 and 7), having an exit port 28 adjacent the second balloon 18 and being dimensioned and adapted for the delivery of a contrast medium through the exit port 28 and into the biliary or urinary tract 100 of the patient. The exit port 28 is shown proximal of the second balloon 18 in FIG. 6, and distal of the second balloon 18 in FIG. 7. However, should the need for a contrast medium arise, it is probably preferred to instead either inject the contrast medium around the guide wire 22, or remove the guide wire 22 from the third lumen 24 and introduce the contrast medium through the third lumen 24. Again, the provision of such aids to imaging may not be particularly preferred, since it is intended that the second balloon 18 and the stone 104 be viewed through the dilated Sphincter of Oddi 102.

Use of the device 10 of the present invention for extracting the stone 104 from the patient can now be easily understood. As mentioned above, the relatively small profile of the device 10 readily allows the catheter shaft 12 and the deflated first and second balloons 14 and 18 to be advanced along a previously inserted guide wire 22, for example, extending through the Sphincter of Oddi 102. Such a position for the guide wire 22 and device 10 is shown in FIG. 1, the endoscope 30 first having been introduced into the patient via an antegrade approach and advanced along the guide wire 22. Once the first balloon 14 lies fully across the Sphincter of Oddi 102, the first balloon 14 is inflated so as to dilate the Sphincter of Oddi 102 (FIG. 3). The first balloon 14 is then deflated so as to allow observation of the second balloon 18 and the stone 104 through the Sphincter of Oddi 102 via the endoscope 30 (FIG. 4). The device 10 is advanced in the direction of arrow 56 until the second balloon 18 has passed the stone 104. The second balloon 18 is then inflated (FIG. 5) and manipulated to urge the stone 104 in the direction of arrows 58 through the Sphincter of Oddi 102 and into the duodenum of the patient. The second balloon 18 is then deflated and the device 10, the endoscope 30 and the guide wire 22 withdrawn from the patient.

Of course, the stone 104 can be manipulated by other structures. More particularly, with additional reference to FIGS. 8 and 9, an embodiment of a device 110 according to the present invention is thereshown, useful for extracting biliary or urinary stones, calculi or the like (such as stone 104) from the biliary or urinary tract 100 of a patient. Like the device 10, the device 110 is most preferably employed for temporary dilation of the Sphincter of Oddi 102 within the biliary tract 100, and will therefore be described with respect to a stone 104 located within the ampulla of Vater 106. Reference to FIG. 1 should be had for the biliary tract 100, the Sphincter of Oddi 102, the stone 104 and the ampulla of Vater 106.

The device 110 of the present invention first comprises a catheter shaft 112 and an inflatable dilation balloon 114 fixed on the catheter shaft 112. The catheter shaft 112 is comparable to the catheter shaft 12 of the device 10, while the balloon 114 is comparable to the first balloon 14 of the device 10. The catheter shaft 112 thus preferably comprises silicone or another suitable medical grade material. When intended for use at the Sphincter of Oddi 102, the catheter shaft 112 is advantageously about 5 to about 7 French (1.67 to 2.33 mm) in size, and when the device 110 is employed via an antegrade approach, the catheter shaft 112 is advantageously about 180 to about 200 cm long.

The balloon 114 is preferably dimensioned and adapted for the temporary dilation of the Sphincter of Oddi 102 from an undilated diameter to a dilated diameter. To this end, the balloon 114 is about 3 to about 6 cm long, and is inflatable to a diameter of about 4 to about 10 mm. The balloon 114 preferably comprises PET or another suitable medical grade material.

The device 110 of the present invention also comprises a reversibly collapsible extraction basket 154 slidably receivable in, and extendable from, the catheter shaft 112. The basket 154 is dimensioned and adapted for urging the stone 104 through the biliary or urinary tract 100 of the patient. Preferably, the basket 154 is dimensioned and adapted for urging the stone 104 through the Sphincter of Oddi 102, after temporary dilation of the Sphincter of Oddi 102 to its dilated diameter by inflation of the balloon 114 and deflation of the balloon 114, and before closure of the Sphincter of Oddi 102 to its undilated diameter. When intended for use in engaging a stone 104 in the ampulla of Vater 106, the basket 154 is advantageously expandable to a diameter of about 0.6 to about 3 cm, and is about 3 to about 6 cm long. The basket 154 preferably comprises a plurality of wires 158, the wires 158 being joined distally by an atraumatic tip 160 on the basket 154.

It is highly desirable that the basket 154 resist kinking during use, that is, during introduction of the device 110 into the patient via an endoscope 30. It is also highly desirable that the basket 154 possesses a predetermined shape when extended from the catheter shaft 112. Accordingly, the wires 158 of the basket 154 preferably comprise a shape memory material, most preferably nitinol in a superelastic state. The properties of nitinol alloy in it superelastic state are well known, and need not be recited here. Other materials include superelastic or pseudoelastic copper alloys such as copper/aluminum/nickel, copper/aluminum/zinc, or copper/zinc As indicated, the basket 154 is slidably receivable in the catheter shaft 112. For this purpose, the catheter shaft 112 includes a longitudinally extending basket lumen 152 defined therein, the basket lumen 152 being dimensioned to receive the basket 154 therein. Preferably, the device 110 of the present invention further comprises an elongated control member 156 on which the basket 154 is mounted. The control member 156 can be a discrete elongate member, or can simply be longitudinally extending portions of the basket wires 158. The control member 156 extends fully through and is slidable in the basket lumen 152; movement of the control member 156 relative to the catheter shaft 112 causes collapse or expansion of the basket 154. Collapse or expansion of the basket 154 may be aided by including a metal sheath 162 in the basket lumen 152, positioned between the catheter shaft 112, and the control member 156 and the basket 154 (FIG. 10). The control member 156 is slidably disposed in the metal sheath 162. When the device 110 is employed for engaging the stone 104 via an antegrade approach through the endoscope 30, the basket 154 and the control member 156 together are advantageously about 220 cm long.

As with the device 10, it is preferred during use of the device 110 that the stone 104 and basket 154 be imaged via the endoscope 30 directly through the temporarily dilated Sphincter of Oddi 102. Of course, depending upon the circumstances of use, it may be desirable to image the catheter shaft 112, the basket 154 and/or the stone 104 by means of radioscopy, fluoroscopy or the like. Accordingly, the catheter shaft may include one or more radiopaque bands (not shown) like the bands 48 and 50 of the device 10. The catheter shaft 112 of the device 110 can also or alternatively include a longitudinally extending contrast lumen defined therein, comparable to the fourth lumen 26 of the device 10. The contrast lumen has an exit port 128 positioned distal of the balloon 114 and is dimensioned and adapted for the delivery of a contrast medium through the exit port 128 and into the biliary or urinary tract 100 of the patient, preferably into the ampulla of Vater 106.

Also as with the device 10, the device 110 can further comprise the endoscope 30 to which the catheter shaft 112 is connectable.

Use of the device 110 of the present invention for extracting a stone 104 from the patient is similar to the use of the device 10 as described above. The endoscope 30 is introduced into the patient. The basket 154 is received in the catheter shaft 112, and the device 110 introduced through the endoscope 30 and manipulated so that the portion of the catheter shaft 112 bearing the balloon 114 on it cannulates and lies fully across the Sphincter of Oddi 102. The balloon 114 is then inflated by connection to a pressurized source 54 of an inflation medium to dilate the Sphincter of Oddi 102. The balloon 114 is then deflated, and the control member 156 moved so as to cause the basket 154 to extend from the catheter shaft 112. The basket 154 is manipulated to engage the stone 104 and urge it towards and out the Sphincter of Oddi 102, and into the patient's duodenum. If the basket 154 has captured the stone 104, the device 110 and endoscope 30 are removed from the patient to complete the extraction of the stone 104 from the patient. If instead the stone 104 is not captured by the basket 154, the stone 104 is allowed to pass naturally from the duodenum.

Both the device 10 and the device 110 provide for both the temporary dilation of a structure in the biliary or urinary tract 100, preferably of the Sphincter of Oddi 102, and the engagement or extraction and removal of stones, calculi or the like, Without requiring removal of the dilation balloon and introduction of another balloon or basket. This significantly shortens the time necessary for the successful performance of the extraction or removal procedure, while avoiding the need to surgically cut the Sphincter of Oddi or other structure in the patient. Without regard to whether the device 10, the device 110 or some prior art apparatus is employed, however, it is important that the dilating balloon be positioned so that inflation of the balloon results in dilation of the sphincter or other structure, rather than resulting in the application of a longitudinal force tending to move the dilating balloon inward or outward of the sphincter or other structure. Since movement of the dilating balloon in the endoscope is generally parallel to the line of sight of the endoscope, viewing of the position of the dilating balloon relative to the sphincter or other structure may be problematic. The present invention also addresses this problem, however.

More particularly, with reference to FIGS. 11 through 13, an embodiment of a device 210 according to the present invention is thereshown, useful for temporarily dilating a sphincter 102 in a patient (not shown). The device 210 is self-centering, such that an appropriate degree of dilation of the sphincter 102 is assured. The device 210 thereby prepares the sphincter for the performance of any desired procedure.

The device 210 of the present invention first comprises an elongated catheter shaft 212 (generally comparable to the catheter shaft 12 of the device 10) and an inflatable balloon 264 carried on the catheter shaft 212. Preferably, the catheter shaft 212 has a proximal end 232 and a distal end 234, and the balloon 264 is affixed to the catheter shaft 212 adjacent to the distal end 234 of the catheter shaft 212.

The balloon 264 comprises a proximal inflatable portion 266, a distal inflatable portion 268 and an intermediate inflatable portion 270 between the proximal and distal portions 266 and 268. The intermediate portion 270 of the balloon 264 has, upon inflation of the balloon 264, a diameter suited for temporary dilation of the sphincter 102 in the patient. The proximal and distal portions 266 and 268 of the balloon 264 have, upon inflation of the balloon 264, diameters greater than the inflated diameter of the intermediate portion 270 of the balloon 264. The intermediate portion 270 of the balloon 264 is thereby automatically centered in the sphincter 102 upon inflation of the balloon 264, the proximal and distal portions 266 and 268 preventing longitudinal movement of the balloon 264 in the sphincter 102.

Preferably, the device 210 of the present invention is dimensioned and adapted for the temporary dilation of the Sphincter of Oddi 102, the inflated diameters of the intermediate, proximal and distal portions 270, 266 and 268 of the balloon 264 being selected to be suited therefor. The balloon 264 preferably comprises nondistendable PET or another suitable medical grade material. Also preferably, the proximal, intermediate and distal portions 266, 270 and 268 of the balloon 264 are in fluid communication with one another. More preferably, the proximal, intermediate and distal portions 266, 270 and 268 of the balloon 264 are continuously formed, such that the balloon 264 has only a single inflation chamber 274 defined in it.

When the device 210 of the present invention is used for the temporary dilation of the Sphincter of Oddi 102, specific dimensions for the balloon 264 can be particularly advantageous. Accordingly, it is preferred that the inflated diameters of the proximal and distal portions 266 and 268 of the balloon 264 are about 2 mm greater than the inflated diameter of the intermediate portion 270 of the balloon 264. More preferably, the inflated diameter of the intermediate portion 270 of the balloon 264 is about 4 to about 8 mm, while the inflated diameters of the proximal and distal portions 266 and 268 of the balloon 264 are about 6 to about 10 mm. The balloon 264 is preferably about 1.5 to about 4 cm long.

The catheter shaft 212 of the device 210 includes at least a first longitudinally extending lumen 216 defined therein. The first lumen 216 is dimensioned and adapted for the supply of a suitable inflation medium to the balloon 264, for example, from a pressurized source 54 of the inflation medium. The catheter shaft 212 also preferably includes a second longitudinally extending lumen 224 defined therein, comparable to the third lumen 24 of the device 10. The second lumen 224 is dimensioned and adapted for receiving a guide wire 222 therethrough. The guide wire 222 can be the same as the guide wire 22 described above. The device 210 can itself further comprise the guide wire 222.

Like the devices 10 and 110, the device 210 of the present invention is useful with an over-the-wire endoscope 30 to which the catheter shaft 212 is connectable. The device 210 can, of course, additionally comprise the endoscope 30. In use, the guide wire 222 is disposed across the Sphincter of Oddi 102, and the endoscope 30 advanced along the guide wire 222 until its distal end lies adjacent the Sphincter of Oddi 102. The device 210 is then positioned on the guide wire 222 and introduced into the endoscope 30, then advanced until the distal end 234 of the catheter shaft 212 lies adjacent to the Sphincter of Oddi 102. The device 210 is advanced further, until the catheter shaft 212 cannulates the Sphincter of Oddi 102 and the balloon 264 lies generally across the it. The balloon 264 is then inflated and dilates the Sphincter of Oddi 102, while automatically centering in it. The balloon 264 is deflated, and the device 210 withdrawn from the patient. An opportunity is thereby provided for the performance of any other desired procedure.

The device 210 can comprise additional features which facilitate cannulation of the Sphincter of Oddi 102. More particularly, the catheter shaft 212 of the device 210 preferably includes a curled tip 272 extending distally of the balloon 264. Advantageously, the curled tip 272 can be about 4 cm long. Moreover, a distal portion 252 of the curled tip 272 of the catheter shaft 212 can be tapered, further aiding passage of the distal end 234 of the catheter shaft 212 into and through the Sphincter of Oddi 102.

Figure 15:
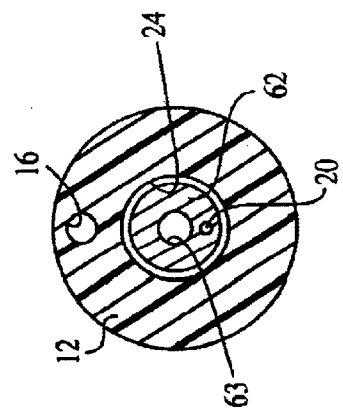
FIG. 15 is a cross-sectional view taken along line 15—15 of FIG. 14.

In the embodiment of FIGS. 14 and 15 a first tube 12 is located outside the second tube 62. First tube 12 has a central axial lumen 24 extending from the proximal end to the distal end of the tube and is dimensioned to receive the second tube 62. In addition to its central lumen 24, first tube 12 has a lumen 16 parallel to and of a smaller diameter than the central axial lumen, for supplying fluid to the balloon 14 (represented inflated), a tapered end 34, a coupling device 36 and an inlet 38 for lumen 16. The second tube 62 has also a central axial lumen 63 and another lumen 20 parallel to and of a smaller diameter than the central axial lumen of tube 62 for supplying fluid to the balloori 18 (represent inflated). Means of supplying fluid for inflating balloons 14 and 18 are provided at the proximal ends of lumens 16 and 20 respectively (not shown). The device is introduced through the working channel of endoscope 30, which also provides means of observing the procedure of dilating the sphincter or tract entrance and retrieving the stone. Without an endoscope, alternative means of imaging the area of the sphincter or opening must be provided during the procedure.

The procedure of dilating the sphincter or tract entrance and retrieving the stones with the telescopic device of FIG. 2 is based on the twostep method described with respect thereto. Firstly, the device is introduced through the working channel of an endoscope 30 up to the region of the sphincter or opening that needs to be dilated. At this stage, the distal extremity of second tube 62 is located proximally with respect to the distal extremity of first tube 12. Under direct vision from the endoscope, the surgeon introduces first tube 12 with balloon 14 deflated within the sphincter or opening. At this stage, balloon 14 is deflated and the first tube is withdrawn from its present position within the sphincter. Balloon 18 at the distal extremity of the second tube is then pushed distally to the distal extremity of the first tube and is introduced through the opened sphincter distally to the partially obstructing stone within the tract of the patient up to its retrieval position. Regarding location of the second apparatus during a retrieval procedure, the second apparatus is to be positioned via the catheter either on the distal side of the stone so that it can draw the stone so that when the second apparatus is a basket or cage, the latter can capture them and then withdraw them towards the sphincter or opening. Either of these positions is to be referred to as a "retrieval position". Balloon 18 is then inflated to its manufactured volume of up to about 4 ml$^3$ and the stones are retrieved by moving the second tube proximally until the stones are retrieved from the tract of the patient.

Figure 16:
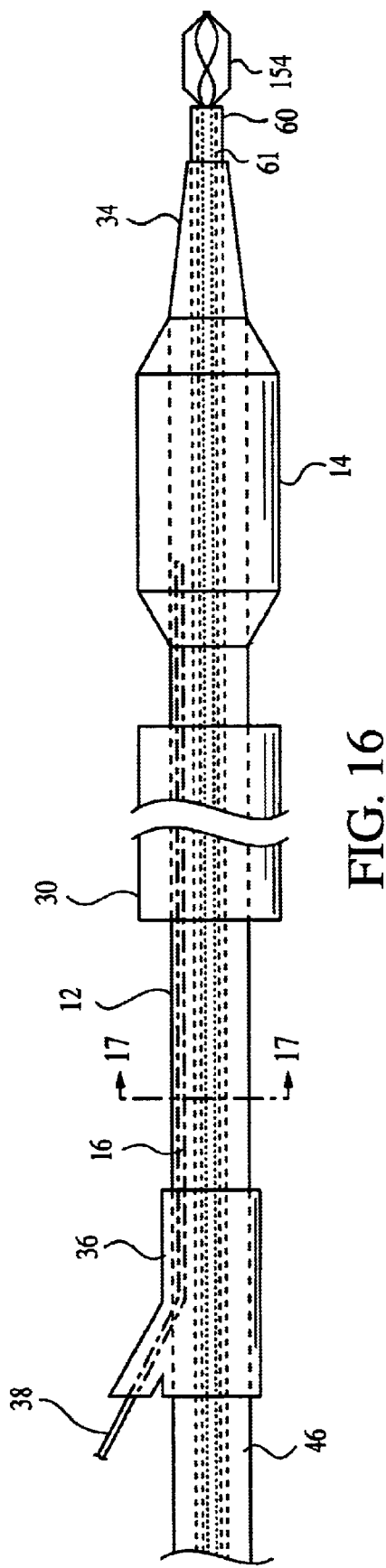
FIG. 16 is a cross-sectional view of another embodiment of the present invention.
Figure 17:
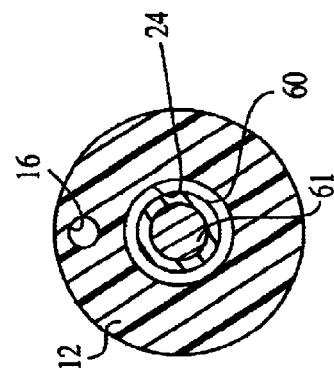
FIG. 17 is a cross-sectional view taken along line 17—17 of FIG. 16.

A further embodiment is shown in FIGS. 16 and 17 that is similar to the embodiment of FIG. 8. Whereas, in FIG. 8 the control member 15 of basket 154 is introduced directly within the lumen of catheter 112, in the embodiment of FIGS. 16 and 17, a second tube 60 is provided within central axial lumen 24 of first tube 12, the second tube having a lumen within which the elongated control member 61 of basket 154 is located. The procedure for stone retrieval is similar to that used with the embodiment of FIG. 8, except that when a retrieval basket or cage is used to retrieve the stone from a tract, the basket or cage has to be positioned adjacent to the stone so that the basket or cage can capture them and then withdraw them toward the sphincter or tract opening.

Figure 18:
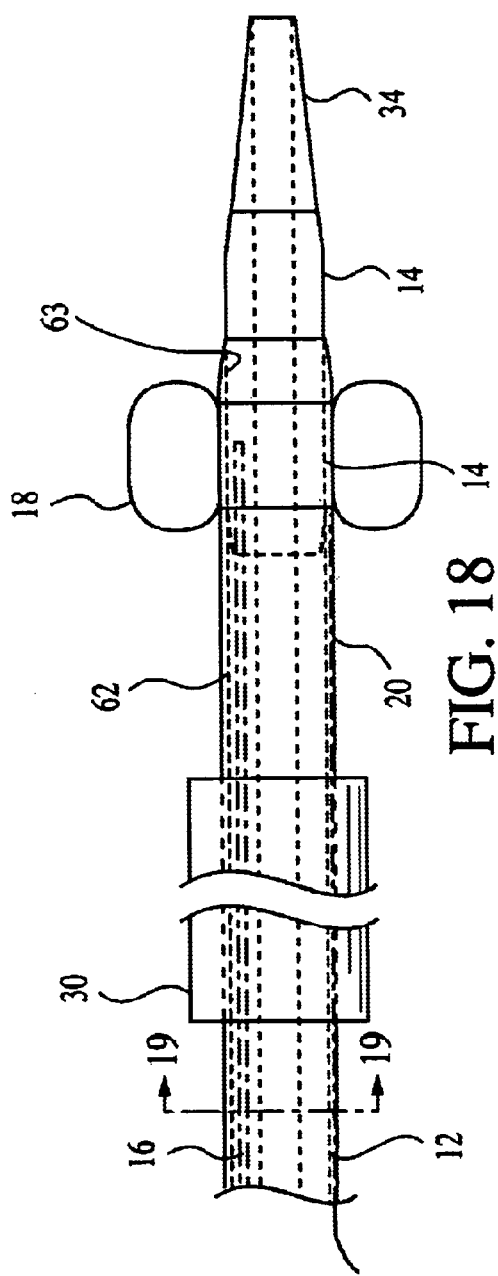
FIG. 18 is a cross-sectional view of another embodiment of the present invention.
Figure 19:
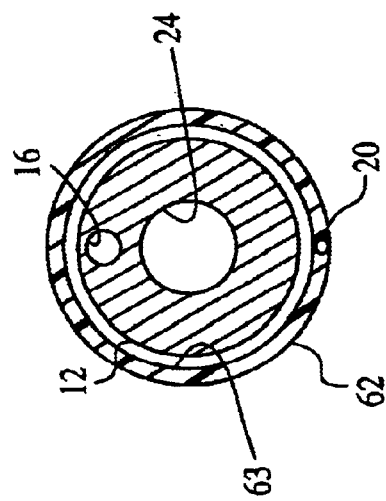
FIG. 19 is a cross-sectional view taken along line 19—19 of FIG. 18.

In the telescopic arrangement of FIGS. 18 and 19, first tube 12 is the inner tube and second tube 62 is the outer tube. In FIG. 18, balloon 14 of first tube 12 is deflated while balloon 18 of second tube 62 is inflated. First tube 12 has a central axial lumen 24 and an additional lumen 16, for supplying fluid to balloon 14, lumen 16 being parallel to and of a smaller diameter than the diameter of lumen 24. The second tube 62 has an axial lumen 63 into which first tube 12 is located and lumen 20 parallel to and of a smaller diameter than the diameter of lumen 20. The two-step method described for the telescopic arrangement of FIG. 14 applies also to the embodiment of FIG. 18.

The twin balloon arrangement of the present application is well suited to a situation when a dilated sphincter or opening closes rapidly after dilation and before a surgeon could proceed to the extraction of the stone.

With a few manipulations, the sphincter could be re-dilated and the extraction procedure continued. Similarly, the proposed telescopic arrangement would be advantageous over today's catheters: the surgeon would be able to maintain the sphincter or entrance opened while proceeding to the extraction of the stone, and were the central lumen of the expanded first apparatus sufficiently large, viewing by the surgeon is enabled for stone capture. Alternatively, were the dilation expansion apparatus a basket or cage, or a balloon formed of transparent material, viewing through the dilation expansion apparatus would be possible when expanded.

In view of the foregoing, it should be clear that the present invention provides devices 10, 110 and 210 for dilating sphincters or other tract entrances in the body, and engaging and extracting or removing stones, calculi or the like from the biliary or urinary tract of a patient. Each of the embodiments of the device of the present invention is particularly advantageous over prior dilation and extraction devices in one or more of a variety of ways. The devices of the present invention may permit the engagement and extraction or removal of stones, calculi or the like from the biliary tract, the urinary tract or other body structure without requiring any surgical cutting of body tissue. The devices of the present invention may also permit the introduction of an associated retrieval basket, extraction balloon or the like quickly enough to take advantage of the time the Sphincter of Oddi or other structure remained dilated, so as to permit the ready passage of the basket or balloon through the Sphincter and allow the ready observation of the engagement of the stones by the basket or balloon via the endoscope. The devices of the present invention may also permit their associated basket, balloon or the like to urge the stones through the Sphincter of Oddi or other structure while it was still dilated. Finally, the devices of the present invention may affirmatively ensure the position of the dilation balloon with respect to the Sphincter of Oddi or other body structure during its dilation.

The details of the construction or composition of the various elements of the devices 10, 110 and 210 of the present invention not otherwise disclosed are not believed to be critical to the achievement of the advantages of the present invention, so long as the elements possess the strength or mechanical properties needed for them to perform as disclosed. The selection of any such details of construction are believed to be well within the ability of one of even rudimentary skills in this area, in view of the present disclosure. For practical reasons, however, the devices 10, 110 and 210 of the present invention should probably be considered to be single-use devices, rather than being reusable.

INDUSTRIAL APPLICABILITY

The present invention is useful for dilating sphincters or other structures in the body of a human or veterinary patient, and engaging and extracting or removing stones, calculi or the like from the body of a human or veterinary patient, for example, from the biliary or urinary tract of the patient, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A device for extracting biliary or urinary stones, calculi or other obstructions from a tract of a patient, comprising:
   a catheter shaft;
   a first expandable apparatus affixed to the catheter shaft and being movable between a collapsed position and an expanded position, the expanded position being adapted for dilating an entrance to the tract; and
   a second expandable apparatus associated with the catheter shaft for urging the stones, calculi or other obstructions through the entrance and from the tract while the entrance of the tract is still dilated;
   wherein the first expandable apparatus is in the collapsed position during movement of the second expandable apparatus to urge the stones, calculi or other obstructions through the entrance and from the tract.

2. A device of claim 1, wherein the second expandable apparatus is an inflatable balloon.

3. A device of claim 1, wherein the second expandable apparatus is a reversibly collapsible extraction basket slidably receivable in and extendable from the catheter shaft.

4. A device of claim 1, wherein the first expandable apparatus is an inflatable balloon.

5. A medical device for extracting stones, calculi or other obstructions from a tract of a human or veterinary patient, wherein the device comprises a catheter; first expandable apparatus on one part of the catheter, the apparatus being positionable within a sphincter or opening associated with said tract and comprising a material that when expanded radially will dilate the sphincter or opening; and second apparatus on another part of the catheter, said another part being distal to said one part, and positionable and expandable radially to permit retrieval at a retrieval position of the stones, calculi or other obstructions while the sphincter or opening is still dilated;
   wherein the catheter comprises a continuous tube with the first and second expandable apparatus connected thereto, and wherein the first expandable apparatus is collapsed during retrieval of the stones, calculi or other obstructions by the second expandable apparatus.

6. A device according to claim 5, wherein the catheter comprises two telescopically arranged tubes movable relative to one another, with the first expandable apparatus connected to a first one of the tubes, and with the second one of the two tubes extending distally beyond the distal end of the first tube, and with the second expandable apparatus connected to the second tube.

7. A device according to claim 5, wherein the first expandable apparatus is a first balloon made of nondistendable material.

8. A device according to claim 7, wherein said nondistendable material is polyethylene or a medical grade material of comparable softness and elasticity.

9. A device according to claim 7, wherein the first balloon is inflatable to a diameter of about 4 to about 10 mm.

10. A device according to claim 5, wherein the second expandable apparatus is a second balloon made of distendable material.

11. A device according to claim 10, wherein said distendable material is latex or a medical grade material of comparable softness and elasticity.

12. A device according to claim 10, wherein the second balloon is inflatable to a diameter of about 8 to about 15 mm, and to a volume of about 1.5 to about 4 cm$^3$.

13. A device according to claim 5, wherein the catheter comprises at least three longitudinally extending lumens, first and second lumens for access respectively to said first and second expandable apparatus, and a third lumen extending from a proximal end to a distal end of said catheter that is dimensioned and adapted for receiving a guide wire therein.

14. A device according to claim 13, wherein the catheter further includes a fourth lumen extending from the proximal end to an exit port near the distal end of said catheter to enable passage of contrast medium to the tract.

15. A device for extracting biliary or urinary stones, calculi or other obstructions from a tract of a patient, comprising:
- a catheter shaft;
- an inflatable balloon fixed on the catheter shaft for temporary dilation of an entrance to the tract; and
- a reversibly collapsible extraction basket slidably receivable in and extendable from the catheter shaft, dimensioned and adapted for urging the stones, calculi or other obstructions through the tract of a patient while the entrance of the tract is still dilated;
- wherein the balloon is deflated following temporary dilation of the entrance to permit the stones, calculi or other obstructions to be urged by the basket through the dilated entrance.

16. The device according to claim 15, wherein the balloon is dimensioned and adapted for the temporary dilation of the Sphincter of Oddi from an undilated diameter to a dilated diameter.

17. The device according to claim 15, wherein the balloon is inflatable to a diameter of about 4 to about 10 mm.

18. The device according to claim 15, wherein the basket is expandable to a diameter of about 0.6 to about 3 cm.

19. The device according to claim 15, wherein the basket comprises a plurality of wires comprising nitinol in a superelastic state.

20. The device according to claim 15, wherein the catheter shaft includes a longitudinally extending basket lumen defined therein, dimensioned to receive the basket therein; and wherein the device further comprises a control member on which the basket is mounted, the control member extending through the basket lumen in the catheter shaft.

21. A device for temporarily dilating a sphincter in a patient, comprising:
- an elongated catheter shaft; and
- an inflatable balloon carried on the catheter shaft, the inflatable balloon comprising a proximal inflatable portion, a distal inflatable portion and an intermediate inflatable portion between the proximal and distal inflatable portions;
- wherein the intermediate inflatable portion has, upon inflation of the balloon, a diameter suited for temporary dilation of the sphincter in the patient; and
- wherein the proximal and distal inflatable portions have, upon inflation of the balloon, diameters greater than the inflated diameter of the intermediate inflatable portion.

22. The device according to claim 21, wherein the device is dimensioned and adapted for temporary dilation of the Sphincter of Oddi, and the inflated diameters of the intermediate, proximal and distal inflatable portions of the balloon are suited for temporary dilation of the Sphincter of Oddi.

23. The device according to claim 21, wherein the proximal, intermediate and distal portions of the inflatable balloon are continuously formed.

24. The device according to claim 21, wherein the inflated diameters of the proximal and distal portions of the balloon are about 2 mm greater than the inflated diameter of the intermediate portion of the balloon.

25. The device according to claim 24, wherein the inflated diameter of the intermediate portion of the balloon is about 4 to about 8 mm.

26. The device according to claim 21, wherein the catheter shaft includes a curled tip extending distally of the inflatable balloon.

27. A medical device for extracting stone or calculi from a tract of a human or veterinary patient, wherein the device comprises a catheter; first expandable apparatus on one part of the catheter, the apparatus being positionable within a sphincter or opening associated with said tract and of a material such that when it is expanded radially it will dilate the sphincter or opening; and second apparatus on another part of the catheter, said other part being distal to said one part, and positionable and expandable radially to permit retrieval at a retrieval position of the stones, calculi or other obstructions;
- wherein the catheter further comprises two telescopically arranged tubes movable relative to one another, with the first expandable apparatus connected to a first one of the tubes, and with the second one of the two tubes extending distally beyond the distal end of the first tube, and with the second expandable apparatus connected to the second tube.

28. A medical device for extracting stone or calculi from a tract of a human or veterinary patient, wherein the device comprises a catheter; first expandable apparatus on one part of the catheter, the apparatus being positionable within a sphincter or opening associated with said tract and of a material such that when it is expanded radially it will dilate the sphincter or opening; and second apparatus on another part of the catheter, said other part being distal to said one part, and positionable and expandable radially to permit retrieval at a retrieval position of the stones, calculi or other obstructions;
- wherein the catheter comprises at least four longitudinally extending lumens, first and second lumens for access respectively to said first and second expandable apparatus, a third lumen extending from a proximal end to a distal end of said catheter that is dimensioned and adapted for receiving a guide wire therein, and a fourth lumen extending from the proximal end to an exit port near the distal end of said catheter to enable passage of contrast medium to the tract.

\* \* \* \* \*